US00PP12524P2

(12) United States Plant Patent
Strope et al.

(10) Patent No.: US PP12,524 P2
(45) Date of Patent: Apr. 9, 2002

(54) INTERSPECIFIC DIANTHUS PLANT NAMED 'ROMANTIC MORN'

(75) Inventors: Kerry Strope, Pismo Beach; Scott Trees, Shell Beach, both of CA (US)

(73) Assignee: Ball Flora Plant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/535,614

(22) Filed: Mar. 27, 2000

(51) Int. Cl.[7] ..... A01H 5/00
(52) U.S. Cl. ..... Plt./263
(58) Field of Search ..... Plt./263, 272

(56) References Cited

PUBLICATIONS

Ball Seed Catalog p. 27 (1997–1998).
*Hortus Third A Concise Dictionary of Plants Cultivated in the United States and Canada*, MacMillan Publishing Company (1976).
Armitage, A., *Greenhouse Grower*, 75–78 (Jun. 1999).
Sparnaaij, L., et al., *Euphytica*, 50:211–220 (1990).
Guobao, W. et al.., *Acta Horticulture*, 404:82–90 (1993).
Gatt, M.K. et al., *Scientia Horticulture*, 77:207–218 (1998).
Simard, M.H., et al., *Plant Cell, Tissue and Organ Culture*, 29:37–42 (1992).
Copy of U.S. application No. 09/817,823—"Interspecific Dianthus Plant" filed on Mar. 26, 2001. Inventors: Kerry Strope and Scott Trees.
Ball Seed Catalog p. 22 (2000–2001).

*Primary Examiner*—Bruce R. Campell
*Assistant Examiner*—June Hwu
(74) *Attorney, Agent, or Firm*—Gardner, Carton & Douglas

(57) ABSTRACT

A new and distinct Dianthus plant named 'Romantic Morn' is provided. This new cultivar was the result of a unique interspecific cross between *Dianthus caespitosus* and *Dianthus barbatus*. More specifically, the female or seed parent of 'Romantic Morn' was an unnamed *Dianthus caespitosus* plant and the male or pollen parent was a *Dianthus barbatus* 'Wee Willie' plant.

1 Drawing Sheet

BACKGROUND OF THE INVENTION

The present invention comprises a new and distinctive Dianthus plant, hereinafter referred to by the cultivar name 'Romantic Morn'. This new cultivar was the result of a unique interspecific cross between *Dianthus caespitosus* and *Dianthus barbatus*. More specifically, the breeding program which resulted in the production of the new cultivar was carried out at Arroyo Grande, Calif. in 1997. The female or seed parent of 'Romantic Morn' was an unnamed *Dianthu caespitosus* plant which exhibits a mounded trailing habit, pale pink to light yellow flowers with non-overlapping petals and medium green linear foliage. The male or pollen parent of 'Romantic Morn' was a pool of pollen from *Dianthus barbatus* 'Wee Willie' mix (unpatented) which exhibits medium pink flowers. The resulting seed was collected and germinated. From the flowering progeny, a plant was selected and initially designated BFP-2081. The parentage of the new cultivar can be summarized as follows:

*Dianthus caespitosus*×*Dianthus barbatus*

Asexual reproduction of the new cultivar by terminal or stem cuttings taken during 1998 and 1999 at Arroyo Grande, Calif., U.S.A. has demonstrated that the characteristics of the new cultivar as herein described are firmly fixed and are retained through successive generations of such asexual propagation.

SUMMARY OF INVENTION

It was found that the cultivar of the present invention:

(a) exhibits a trailing habit, (b) forms bright pink flowers, (c) exhibits a vigorous growth habit and (d) is extremely floriferous.

The 'Romantic Morn' cultivar has not been observed under all possible environmental conditions to date. Accordingly, it is possible that the phenotype may vary somewhat with variations in the environment, such as temperature, light intensity, and day length.

When the new cultivar of the present invention is compared to the plant *Dianthus deltoides* plant 'Zing Rose' (unpatented), it is found that the new cultivar exhibits longer internodes, longer, narrower leaves, smaller petals, lighter colored flowers.

BRIEF DESCRIPTION OF THE PHOTOGRAPH

The accompanying photographs show as nearly true as it is reasonably possible to make the same in color illustrations of this type, typical flower and foliage characteristics of the new cultivar. The plants were grown in a greenhouse at West Chicago, IL, USA.

DETAILED BOTANICAL DESCRIPTION

The chart used in the identification of colors described herein is The R.H.S. Colour Chart of The Royal Horticultural Society, London, England. The color values were determined on Mar. 14, 2000 in West Chicago, Ill. The readings were taken between 1:00 and 1:45 pm. under approximately 2500 footcandles of light. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night. Plants used for the following descriptions and measurements were grown for 16 weeks after planting of rooted cuttings.

Botanical classification: *Dianthus caespitosus*×*Dianthus barbatus* cultivar 'Romantic Morn'.

Commercial classification: Dianthus hybrid.

Propagation:

*Type cutting.*—Terminal tip.

*Time to initiate roots.*—Approximately 14–21 days with the shorter times generally being experienced in the summer and the longer times in the winter.

*Root description.*—Fibrous, branching.

Plant description:

*General appearance and form.*—Trailing.

*Plant height.*—17 cm.

*Plant width.*—40 cm.

*Length from top of pot to bottom of foliage.*—33 cm.

*Branching habit.*—Freely branching without pinching or growth regulators.

*Branch diameter.*—Approximately 2 mm.

*Internode length.*—Approximately 4.2 cm.

*Stem color.*—137C.

Foliage description:

*Leaf base.*—Sessile.

*Leaf apex.*—Acute.

*Form.*—Linear.

*Margin.*—Entire.

*Arrangement.*—Opposite.

*Venation pattern.*—Parallel.

*Surface.*—Both upper and lower surfaces are smooth.

*Color of mature foliage.*—upper surface.—137A.

*Color of mature foliage.*—lower surface.—137B.

*Size.*—Approximately 5.3 cm in length; approximately 0.4 cm in width.

Flower description:

*Flowering habit.*—'Romantic Morn' is freely flowering under outdoor growing conditions with substantially continuous blooming from spring until fall.

*Flower arrangement.*—Paniculate.

*Flower form.*—Single.

*Flower size.*—Approximately 2.4 cm in diameter.

*Number of petals.*—Five.

*Petal texture.*—Smooth.

*Petal shape.*—Broad limb attenuated into elongated claw.

*Petal margin.*—Sides-entire; tip-fringed.

*Petal apex.*—Rounded.

*Petal length.*—3.2 cm (limb — 1.3 cm; claw — 1.9 c).

*Petal width.*—Limb — 8 mm; claw — 1 mm.

*Flower color.*—Upper surface; When opening: upper surface of petals is closest to 71C, lower surface is closest to 70C. When fully open: upper surface is closest to 68A, lower surface is closest to between 75B and 73C.

*Flower bud shape.*—Cylindrical.

*Flower bud length.*—2 cm.

*Flower bud diameter.*—3 mm.

*Calyx.*—Shape: tubular. Length: 1.9 cm. Diamter: 4 mm. Sepal number: 5. Sepal size: 2 mm wide. Sepal color: Upper surface is between 137 C and 137D. Lower surface is closest to 144A. Sepal surface: Both upper and lower surfaces are smooth.

*Epicalyx.*—Two pairs of scales; Length: 9 mm. Apex: Acute. Surface: Upper and lower surface: Smooth. Color: Upper surface — 137A. Lower surface — 137B.

*Reproductive organs.*—Androecium: 10 stamens, 12 mm in length. Filaments are 155D. Anthers approximately 2 mm in length, closest to 199C in color. Gynoecium: One pistil, approximately 3 cm long. Stigma is two lobed, 155D with fringe. Ovary color is closest to 145A.

*Seed production.*—Seed Production has not been observed.

*Disease resistance.*—None observed.

What is claimed is:

1. A new and distinct Dianthus plant named 'Romantic Morn' substantially as herein shown and described, which:

(a) exhibits a trailing growth habit, (b) forms bright pink flowers, (c) exhibits a vigorous habit and (d) is extremely floriferous.

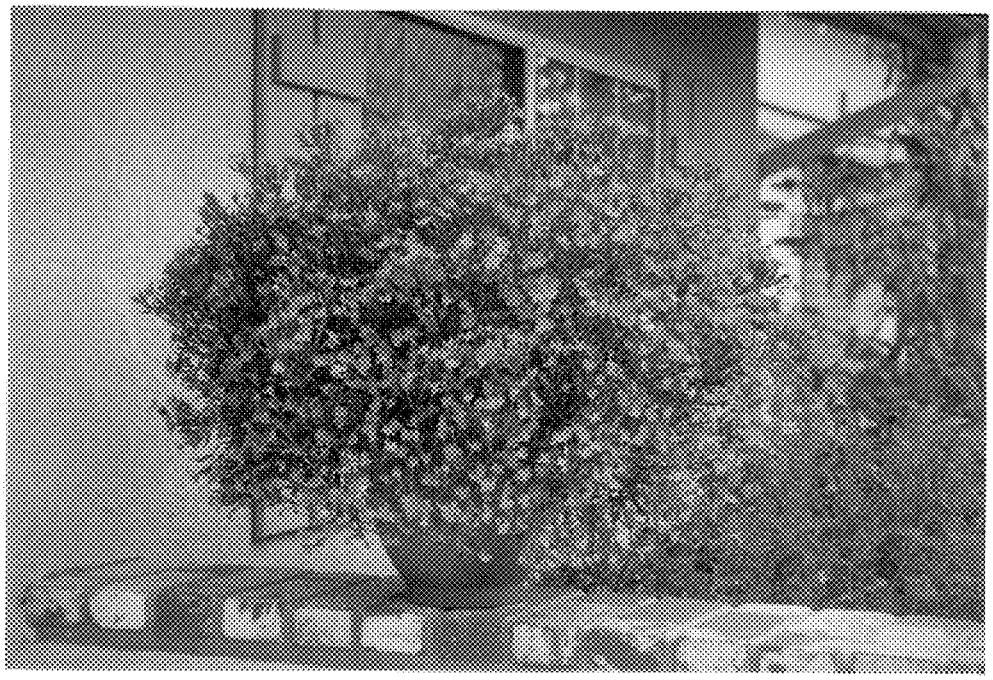

* * * * *